United States Patent
Li et al.

(10) Patent No.: US 7,684,036 B2
(45) Date of Patent: Mar. 23, 2010

(54) METHOD FOR REAL TIME CURE STATUS MONITORING OF DENTAL RESIN

(75) Inventors: Qun Li, Newark, DE (US); Sean Xiaolu Wang, Wilmington, DE (US)

(73) Assignee: BWT Property, Inc., Newark, DE (US)

( * ) Notice: Subject to any disclaimer, the term of this patent is extended or adjusted under 35 U.S.C. 154(b) by 197 days.

(21) Appl. No.: 11/945,324

(22) Filed: Nov. 27, 2007

(65) Prior Publication Data

US 2008/0305459 A1    Dec. 11, 2008

Related U.S. Application Data

(60) Provisional application No. 60/867,958, filed on Nov. 30, 2006.

(51) Int. Cl.
*G01N 21/64* (2006.01)

(52) U.S. Cl. ...................................... 356/318; 356/417

(58) Field of Classification Search .................. 356/318
See application file for complete search history.

(56) References Cited

U.S. PATENT DOCUMENTS 7,245,371 B2    7/2007    Wang et al.

*Primary Examiner*—F. L Evans

(57) ABSTRACT

A method is disclosed for monitoring the curing status of a dental resin through the inherent fluorescence of the dental resin under a curing light. The method requires no sample preparation and is fast enough for real time cure monitoring.

5 Claims, 3 Drawing Sheets

US 7,684,036 B2

METHOD FOR REAL TIME CURE STATUS MONITORING OF DENTAL RESIN

REFERENCE TO RELATED APPLICATIONS

This application claims an invention which was disclosed in Provisional Patent Application No. 60/867,958, filed Nov. 30, 2006, entitled "Method for Real time Cure Status Monitoring of Dental Resin." The benefit under 35 USC §119(e) of the above mentioned U.S. Provisional Applications is hereby claimed, and the aforementioned applications are hereby incorporated herein by reference.

FIELD OF THE INVENTION

This invention generally relates to a method for dental resin cure monitoring, and more specifically to a method for monitoring the curing status of a dental resin through the inherent fluorescence of the dental resin under a curing light.

BACKGROUND

The use of photo-curable dental composite resins is now standard in contemporary dental practice. Such dental composites consist of a mixture of liquid acrylic monomers, particulate fillers such as glass or ceramic particles, and a photo-initiator such as camphorquinone (CQ) that forms a workable composition. This composition can be cured into a hardened filling by activating the photo-initiator via an external light source, which raises it from the ground state to an excited, activated state. After combining with an amine co-initiator, an aminoalkyl free radical is formed which initiates polymerization. The mechanical properties of the cured composite resins were shown to be dependent on the curing process. It is thus highly desirable to monitor the curing status of the resin in real time as to achieve the optimum performance. However, conventional cure monitoring methods such as Raman or FTIR spectroscopy either are too slow or require sample preparation. Fluorescence spectroscopy was proposed before for real time cure monitoring. However, it generally requires a fluorescence probe to be added into the resin. In additional, all these methods require an additional light source for measuring the optical spectrum of the dental resin, which limits their practical application.

There thus exists a need for an improved method for monitoring the curing status of a dental resin. This method should require no sample preparation and be fast enough for real time cure monitoring.

SUMMARY OF THE INVENTION

According to one aspect of the present invention, the inherent fluorescence of a dental resin, which is produced by the curing light, is utilized to monitor the curing status, i.e. the polymerization degree of the dental resin.

According to another aspect of the present invention, the curing status of the dental resin, which is measured from the fluorescence signal, is utilized for feedback control of the curing light to achieve the optimum curing result.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
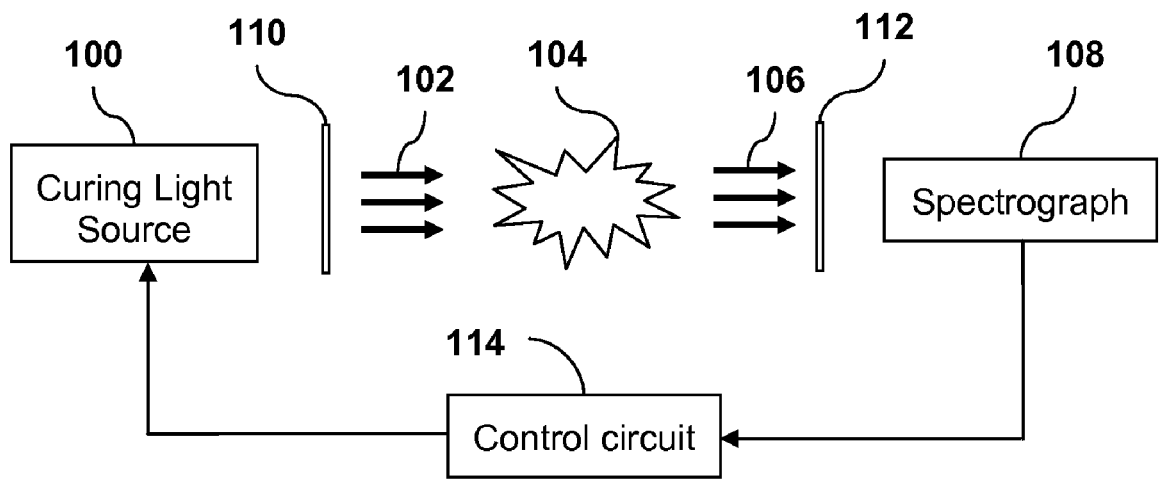
FIG. 1 illustrates a block diagram for the dental resin cure monitoring method.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a method for monitoring the curing status of a dental resin through the inherent fluorescence of the dental resin under a curing light. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

FIG. 1 illustrates one preferred embodiment of the present invention. A curing light source 100 produces a curing light 102 that activates the photo-initiator in a dental resin 104 to trigger the polymerization reaction. Here the curing light source may comprise halogen lamps, light emitting diodes (LEDs) or lasers. During the photo curing process, a fluorescence signal 106 is produced by the dental resin 104. The optical spectrum of the fluorescence signal 106 is measured by a spectrograph 108. The intensity, wavelength distribution of the obtained fluorescence spectrum is then used as an indicator of the degree of conversion for the polymerization reaction. Optical filters 110 and 112 may be applied at the output end of the curing light source 100 and before the spectrograph 108 to help separate fluorescence signal from the scattered curing light. The curing status of the dental resin as measured by the spectrograph can be used to control the output power, duration, or other parameters of the curing light source 100 through a control circuit 114 to achieve the optimum curing results.

In one example of the present embodiment, the curing light source comprises a diode pumped solid state laser with an output wavelength of 473 nm. A shade A3.5 TPH3 micro-matrix restorative resin from Dentsply International is used as the sample dental resin. The fluorescence signal produced by the resin during cure process is measured by a CCD array spectrometer (BTC112E from B&W Tek, Inc.) with a spectral coverage of 200-1050 nm for real time spectrum analysis. The integration time of the spectrometer is set at 40 ms, i.e. it completes one spectrum measurement within 40 ms.

Figure 2A:
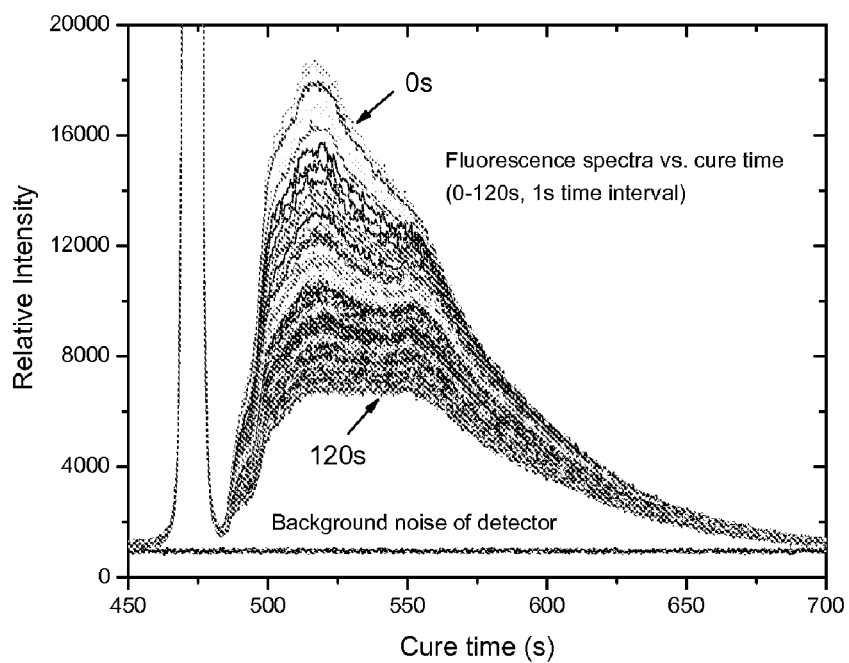
FIG. 2a shows the measured fluorescence spectra of a shade A3.5 TPH3 dental resin, which is cured under a 473 nm blue laser.
Figure 2B:
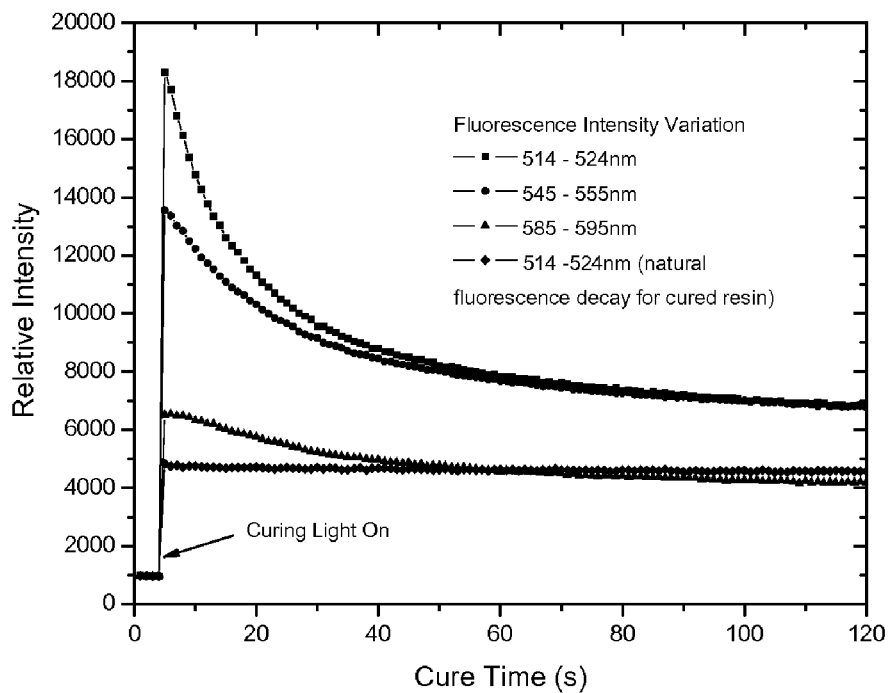
FIG. 2b shows a comparison of polymerization induced fluorescence intensity decay with natural quenching of fluorescence signal for the dental resin.

FIG. 2a shows the variation of the fluorescence spectra for the TPH3 dental resin during a 120 s cure process. The spectra are measured at a 1 s time interval. From FIG. 2a, it can be clearly seen that the inherent fluorescence signal of the dental resin decreases significantly as the resin is cured. This fluorescence signal reduction is accompanied by a change in the shape of the fluorescence spectra. This cure induced fluorescence signal decay is further illustrated in FIG. 2b, where the fluorescence intensity at three characteristic wavelength regions of 514-524 nm, 545-555 nm and 585-595 nm are recorded in respect to the cure time. For comparison purposes, the natural quenching of the fluorescence signal by the same laser for a fully cured TPH3 dental resin is also illustrated in the figure. From FIG. 2b, it can be seen that the cure induced fluorescence decay is most prominent at 514-524 nm. At longer wavelengths, the decay is less significant. But it is still much stronger than the natural quenching of the fluorescence signal. This indicates that the fluorescence decay is closely related to the curing process. Similar fluorescence decay was observed on other branded composite resins such as Vit-1-escence from Ultradent Products, Inc. This fluorescence decay is attributed to the status change of the photo initiator during the polymerization process. Further investigations show that the fluorescence decay rate is influenced by the shade, thickness, filler size, material, and other parameters of the resin, which determine the cure speed of the resin.

Figure 3A:
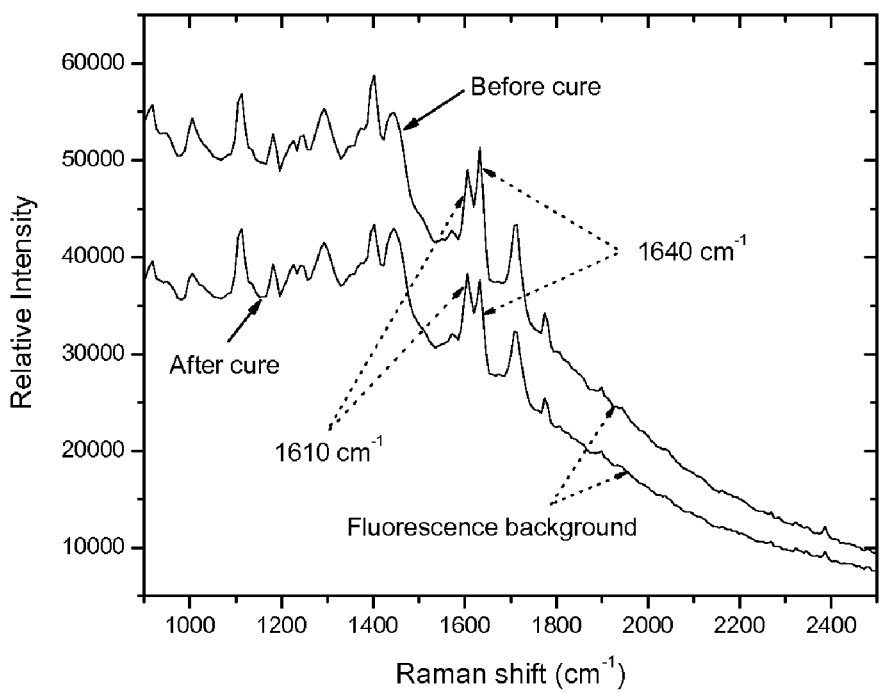
FIG. 3a shows the measured Raman/fluorescence spectra of the dental resin before and after the curing process.
Figure 3B:
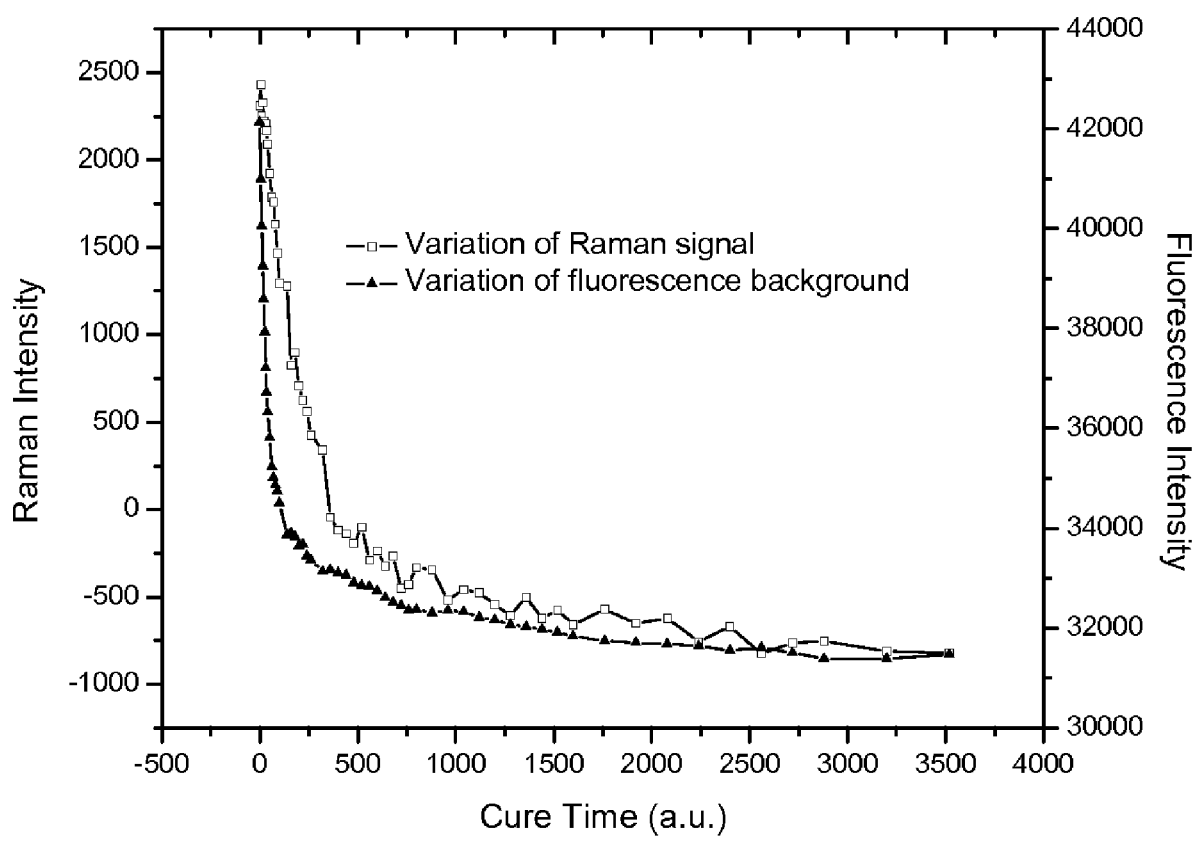
FIG. 3b shows the measured intensity variation of the Raman and fluorescence signal during the cure process.

The method is further verified by measuring the Raman/fluorescence spectra of the resin with a 785 nm laser as the excitation light source. Here the dental resin was cured by an LED light source with a central wavelength of 470 nm and a FWHM bandwidth of about 20 nm. The curing was performed in a stepwise manner and the Raman/fluorescence spectra were measured at the interval of each step. The power of the 785 nm laser was kept at a low level to avoid any additional curing. FIG. 3a shows the measured Raman/fluorescence spectra of the dental resin before and after the curing process. A variation in the relative intensity of the 1610 cm$^{-1}$ and 1640 cm$^{-1}$ Raman band is used as an indicator of the degree of conversion for the dental resin as disclosed by W. S. Shin et al. in "Determination of the degree of cure of dental resins using Raman and FT-Raman spectroscopy," Dental Material, vol. 9, no. 5, pp. 317-24, 1993, which is hereby incorporated herein by reference. In the mean time, the average intensity of the fluorescence background is recorded for each curing step. The result is further illustrated in FIG. 2b. It can be seen that the fluorescence decay of the dental resin shows good consistency with the variation of the Raman signal during the cure process, which verifies the fluorescence method for dental resin cure monitoring.

In the foregoing specification, specific embodiments of the present invention have been described. However, one of ordinary skill in the art appreciates that various modifications and changes can be made without departing from the scope of the present invention as set forth in the claims below. The numerical values cited in the specific embodiment are illustrative rather than limiting. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A method for monitoring the polymerization status of a dental composite resin, the method comprising the steps of:
   causing a light beam to be incident on the dental resin, the light beam having a wavelength selected to cure the dental resin and to excite inherent fluorescence emission from said dental resin;
   measuring a spectrum of said fluorescence emission in real time; and
   obtaining polymerization status information regarding the curing process from the measured fluorescence spectrum.

2. The method of claim 1, wherein the light beam is produced by lamps, light emitting diodes (LEDs), or lasers.

3. A method for optimizing the polymerization result of a dental composite resin, the method comprising the steps of:
   causing a light beam to be incident on the dental resin, the light beam having a wavelength selected to cure the dental resin and to excite inherent fluorescence emission from said dental resin;
   measuring a spectrum of said fluorescence emission in real time;
   obtaining polymerization status information regarding the curing process from the measured fluorescence spectrum; and
   controlling properties of the light beam according to said polymerization status information to achieve the optimum polymerization result.

4. The method of claim 3, wherein the light beam is produced by lamps, light emitting diodes (LEDs), or lasers.

5. The method of claim 3, wherein the properties of the light beam include the intensity and time duration of the light beam.

* * * * *